US00PP28269P3

(12) United States Plant Patent
Sheehan

(10) Patent No.: US PP28,269 P3
(45) Date of Patent: Aug. 15, 2017

(54) GRAPEVINE PLANT NAMED 'SHEEGENE 25'

(50) Latin Name: *Vitis vinifera*
Varietal Denomination: Sheegene 25

(71) Applicant: Sheehan Genetics, LLC, Fresno, CA (US)

(72) Inventor: Timothy P. Sheehan, Vancouver, WA (US)

(73) Assignee: Sheehan Genetics, LLC, Fresno, CA (US)

( * ) Notice: Subject to any disclaimer, the term of this patent is extended or adjusted under 35 U.S.C. 154(b) by 0 days.

(21) Appl. No.: 14/756,740

(22) Filed: Oct. 6, 2015

(65) Prior Publication Data

US 2017/0099759 P1 Apr. 6, 2017

(51) Int. Cl.
*A01H 5/08* (2006.01)

(52) U.S. Cl.
USPC ..... Plt./205

(58) Field of Classification Search
USPC ..... Plt./205
See application file for complete search history.

(56) References Cited

U.S. PATENT DOCUMENTS

| | | | |
|---|---|---|---|
| PP4,787 | P | 11/1981 | Olmo et al. |
| PP9,865 | P | 4/1997 | Ralli et al. |
| PP18,937 | P2 | 6/2008 | Sheehan |
| PP18,959 | P2 | 6/2008 | Sheehan |
| PP18,960 | P2 | 6/2008 | Sheehan |
| PP18,987 | P2 | 6/2008 | Sheehan |
| PP19,041 | P2 | 7/2008 | Sheehan |
| PP19,911 | P2 | 4/2009 | Sheehan |
| PP19,912 | P2 | 4/2009 | Sheehan |
| PP20,110 | P3 | 6/2009 | Sheehan |
| PP20,236 | P3 | 8/2009 | Sheehan |
| PP20,252 | P3 | 9/2009 | Sheehan |
| PP20,281 | P3 | 9/2009 | Sheehan |
| PP20,317 | P3 | 9/2009 | Sheehan |
| PP20,753 | P3 | 2/2010 | Sheehan |
| PP21,316 | P3 | 9/2010 | Sheehan |
| PP23,125 | P2 | 10/2012 | Sheehan |
| PP23,837 | P3 | 8/2013 | Sheehan |
| PP25,095 | P3 | 11/2014 | Sheehan |
| PP25,131 | P3 | 12/2014 | Sheehan |
| 2008/0201809 | P1 | 8/2008 | Sheehan |
| 2013/0276181 | P1 | 10/2013 | Sheehan |
| 2015/0121579 | P1 | 4/2015 | Sheehan |

FOREIGN PATENT DOCUMENTS

| | | |
|---|---|---|
| ES | 20140340 | 11/2014 |
| ES | 2015/1720 | 7/2015 |

OTHER PUBLICATIONS

Boletin Del Registro De Variedades Comerciales Boletin No. Jun. 2014 (Dec. 15, 2014).*
Commercial Production Licence [sic] Agreement, dated Mar. 19, 2015.

* cited by examiner

*Primary Examiner* — Annette Para
(74) *Attorney, Agent, or Firm* — Dentons US LLP

(57) ABSTRACT

A new and distinct grapevine plant named 'Sheegene 25', characterized by the following unique combination of characteristics: 'Sheegene 25' a cultivar developed as a table grape having berries that are large, red, and seedless. The large berries are approximately 7 g each naturally and without girdling or application of plant growth regulators. Harvest is during August when maturity reaches 17-22° brix.

1 Drawing Sheet

Latin name of the genus and species of the plant claimed: *Vitis vinifera.*

Variety denomination: 'Sheegene 25'.

BACKGROUND OF THE INVENTION

The present invention relates to a new and distinct variety of grapevine named 'Sheegene 25'. 'Sheegene 25' produces large, red, seedless grapes on bunches for use as a table grape. The variety originated from a cross of 'Princess' (unpatented) as the pollen parent and 'Red Globe' (U.S. Plant Pat. No. 4,787) as the seed parent. 'Sheegene 25' was asexually propagated in the dormant season of 2004 by grafting on Thompson 2A, virus free rootstock, in a *Vitis vinifera* variety block located near McFarland, Calif. All characteristics and distinctions remain true to form and are established and transmitted through succeeding propagations.

SUMMARY OF THE INVENTION

The present invention relates to a new and distinct grapevine plant, which will hereinafter be denominated as 'Sheegene 25'. 'Sheegene 25' produces large berries averaging 7 g per berry without girdling or application of plant growth regulators. The berries are harvested in August when maturity reaches 17-22° brix. Comparison can be made to 'Scarlet Royal' (U.S. Plant Pat. No. 16,229), 'Crimson Seedless' (unpatented), and 'Ruby Seedless' (unpatented), all of which are also red, seedless cultivars that harvest during the same period in August in the San Joaquin Valley. 'Sheegene 25' is distinct from these cultivars in a number of ways, the most obvious of which are as follows:

Berry Size: 'Sheegene 25' berries are very large, weighing 7 g. 'Crimson Seedless', 'Scarlet Royal', and 'Ruby Seedless' berries are smaller, weighing 4.5 g, 5.8 g, and 3.0 g, respectively.

Berry Shape: 'Sheegene 25' berries are uniquely truncate in shape, whereas 'Crimson Seedless' and 'Scarlet Royal' are ovoid, and 'Ruby Seedless' is round.

Cluster Density: 'Sheegene 25' clusters are medium to loose, whereas 'Scarlet Royal' and 'Ruby Seedless' are tight and usually require berry thinning to loosen the cluster. 'Crimson Seedless' clusters are of medium density with berry thinning required in some years.

Leaves: The leaves of 'Sheegene 25' are pentagonal with deeply lobed lateral sinuses. 'Scarlet Royal' and 'Ruby Seedless' and, to a lesser degree, 'Crimson Seedless' have lateral sinuses that are much less deeply lobed.

'Sheegene 25' can be distinguished from its parent cultivars based on at least the following characteristics:

Seeds: No seeds are present on the berries of 'Sheegene 25', whereas parent cultivar 'Red Globe' is seeded.

Color of Berry Skin: 'Sheegene 25' berries are red in color, whereas parent cultivar 'Princess' berries are yellow-green in color.

'Sheegene 25' can be distinguished from its sibling cultivars based on at least the following characteristics:

Tendril Form: 'Sheegene 25' tendrils are 50% bifid and 50% trifid, whereas sibling cultivars 'Sheegene-3', -9', -12', -13', -17', -18', and -21' tendrils are entirely bifid, sibling cultivar 'Sheegene-1' tendrils are bifid and occasionally trifid, sibling cultivar 'Sheegene-22' tendrils are trifid and occasionally trifid, and sibling cultivar 'Sheegene-24' tendrils are 50% trifid and 50% quadrifid.

Berry Shape: 'Sheegene 25' berries are truncate, whereas sibling cultivars 'Sheegene-1', -3', -9', -12', -13', -17', -18', and -21' berries are ovate, and sibling cultivars 'Sheegene-22 and -24' berries are broad ellipsoid.

BRIEF DESCRIPTION OF THE DRAWINGS

'Sheegene 25' is illustrated by the accompanying photograph, taken of a 5-year-old vine, which shows the plant's vines, foliage, and fruit. The colors shown are as true as can be reasonably obtained by conventional photographic procedures.

The FIGURE shows the typical vegetative morphology of stems, leaves, and tendrils.

DETAILED BOTANICAL DESCRIPTION

Phenotypic Description of *Vitis vinifera* 'Sheegene 25', obtained from 5-year-old plants growing in Delano, Calif. The colors (except those in common terms) are described using the Munsell Color Charts for Plant Tissue by Munsell Color, 617 Little Britain Rd., New Windsor, N.Y. 12553-6148, 1977 revision.

Classification:

*Family*.—Vitaceae.

*Botanical name*.—*Vitis vinifera*.

Plant:

*Plant habit and growth*.—High vigor, semi-erect growth, lateral shoots plentiful.

*Size*.—Age at maturity: Four years. Height (at maturity): Canopy height, 230 cm. Width (at maturity): Canopy width, 250 cm. Vigor: High. Productivity: Medium.

Trunk:

*Diameter*.—10.3 cm.

*Surface texture*.—Rough.

*Color*.—Interior 2.5 YR 4/6; exterior 7.5 YR 5/2.

Canes:

*Size*.—Diameter: 11 mm. Length: 140 cm.

*Surface texture* (*mature cane*).—Smooth, finely ribbed.

*Surface texture* (*immature cane*).—Smooth, very finely ribbed.

*Form* (*woody shoot cross section form*).—Pith in center with diaphragm at node.

*Color* (*mature*).—7.5 YR 6/6 at 20 weeks of age.

*Color* (*immature*).—5 GY 7/6 at 5 weeks of age.

*Internode length* (*upper mature sun cane*).—10 cm.

Time of bud burst: Begin the first week of March; 50% budbreak by mid-March.

Tendrils:

*Form*.—Straight, 50% bifid; 50% trifid.

*Size*.—Medium-long.

*Length*.—21 to 30 cm; mostly 30 cm.

*Diameter*.—3.5 mm at base.

*Texture and distribution*.—Smooth, discontinuous.

*Color* (*mature*).—2.5 GY 7/8 at 4 weeks of age.

*Anthocyanin* (*mature*).—Absent.

*Color* (*immature*).—5 Y 7/8 at 1 week of age.

*Anthocyanin* (*immature*).—Present, 10 R 4/8 toward base.

Growing tips (young shoot):

*Pubescence*.—Absent.

*Light cobweb*.—Present, color 2.5 GY 7/6.

*Anthocyanin*.—Slight presence, color 10 R 5/8.

*Shape*.—Wide open, flat fan.

*Apex*.—Triangular, normal.

Leaves:

*Shape*.—Pentagonal, deeply lobed lateral sinuses.

*Apex*.—Pointed.

*Base*.—Rounded.

*Margin*.—Teeth irregular.

*Length of teeth on margin*.—2 to 10 mm.

*Shape of teeth on margin*.—Both sides straight, pointed.

*Texture* (*mature leaf*).—Upper surface: Smooth, some bullation on outer edges. Lower surface: Smooth, glabrous.

*Size*.—Immature, length: 5.5 cm at 10 days of age. Immature, width: 5.8 cm at 10 days of age. Mature, length: 12 cm at 20 days of age. Mature, width: 15 cm at 20 days of age.

*Color, immature leaf*.—Upper surface: 5 GY 4/8. Lower surface: 5 GY 6/4.

*Color, mature leaf*.—Upper surface: 5 GY 4/4. Lower surface: 5 GY 5/4.

*Venation*.—Pattern: Primary and secondary veins on upper surface are raised; on lower surface veins are raised but not as prominently as on the upper surface. Color: Upper surface: 2.5 GY 6/6. Lower surface: 2.5 GY 8/8.

*Petiolar sinus*.—Mostly half open.

*Petiole*.—Length: 9 to 14 cm. Diameter: 2.5 mm at middle. Color: 2.5 GY 8/8; Anthocyanin 5 R 5/6.

Floral cluster:

*General description and location*.—Small, carrot shape, very small shoulders, inflorescence mostly located on 4th node.

*Quantity of inflorescences per cluster*.—330.

*Size*.—Length: 12 to 16 cm long, not including peduncle. Width: 7 to 12 cm wide, shoulders spread.

*Peduncle length*.—5 to 7 cm.

*Inflorescences*.—Hermaphroditic.

*Stamens*.—Straight, 2 mm in length.

*Anthers*.—Small, not distinct.

*Date of bloom*.—Bloom start, Apr. 22, 2014; Bloom 80%, Apr. 27, 2014; Bloom end, Apr. 30, 2014.

*Pollen amount*.—Abundant, milky yellow, 2.5 Y 8/4.

*Calyptra*.—5 segments, complete separation.

*Calyptra color*.—5 GY 5/6; Anthocyanin pigment on distal end, 2.5 R 5/8.

Fruit:

*Time of year of commercial harvest and shipment*.—Early August to Early September.

*Cluster* (*primary bunches*).—General size: Large, 750 g. Length (without peduncle): 25 cm. Width: Hanging, 17 cm; shoulders spread, 27 cm. Density: Medium-loose. Peduncle length: 7 cm. Peduncle diameter: 6 mm at middle. Peduncle color: 5 GY 6/8. Number of berries per cluster: 102. Berry: Size: Large, 7 g. Shape: Truncate. Uniformity: Very uniform. Brix content: 17.4 on Aug. 13, 2014. Size: Diameter: 18 mm. Length: 30 mm. Skin color: 2.5 R 4/6. Pedicel: Length: 10 mm. Diameter: 2 mm. Color: 5 GY 7/6. Strength of attachment to berry: Strong.

*Cluster* (*secondary bunches*).—Generally size: small/medium/large: Medium, 123 g. Length (without peduncle): 10 cm. Width: Hanging: 10 cm; shoulders spread: 15 cm. Density: loose/medium/tight? Loose. Peduncle length: 11 cm. Peduncle diameter: 3 mm. Peduncle color: 5 GY 6/8. Number of berries per cluster: 20. Berry: Size: Large, 6 g. Shape: Ovoid. Uniformity: Very uniform. Brix content: 17.8 on August 13, 2014. Diameter: 20 mm. Length: 27 mm. Skin color: 5 R 3/6. Pedicel: Length: 8 mm. Diameter: 2 mm. Color: 5 GY 6/8. Strength of attachment to berry: Strong.

Berry flesh:

*Color*.—Creamy white, 2.5 GY 8/4.

*Juice color*.—Clear.

*Juice production*.—Moderate.

*Thickness of skin*.—Medium.

*Flavor*.—Neutral.

*Fragrance*.—Neutral.

*Texture*.—Medium-firm.

*Seeds*.—Absent; no seed rudiments.

*Use*.—Fresh, table grape.

Disease and insect resistance: Disease and insect resistance are typical of the species.

What is claimed is:

1. A new and distinct grapevine plant as described and illustrated herein.

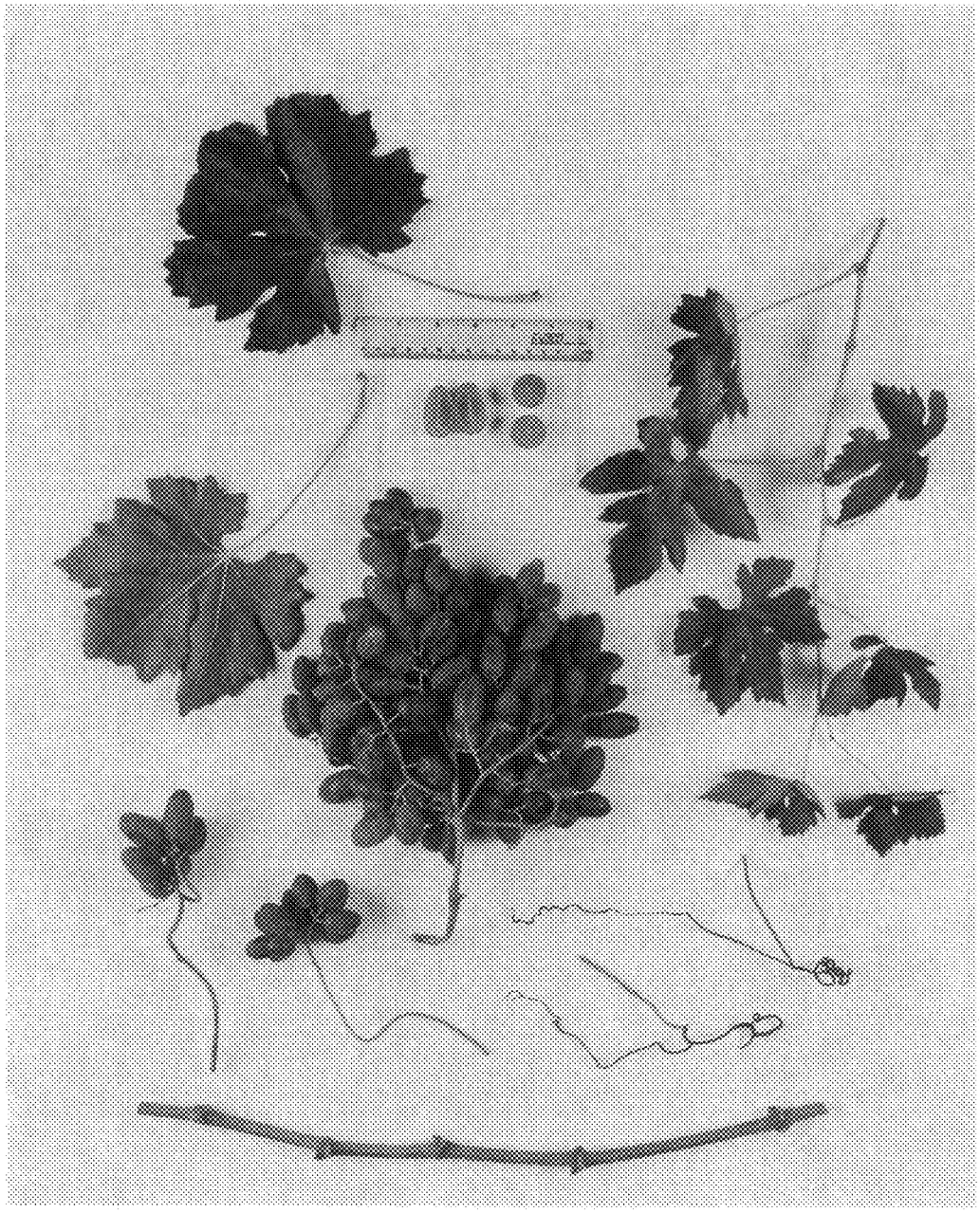

* * * * *